United States Patent [19]
Ellis et al.

[11] Patent Number: 4,812,559
[45] Date of Patent: Mar. 14, 1989

[54] VACCINE AGAINST VARICELLA-ZOSTER VIRUS

[75] Inventors: Ronald W. Ellis, Overbrook Hills; Paul M. Keller, Lansdale; Robert S. Lowe, Harleysville, all of Pa.; Andrew J. Davison, Glasgow, Scotland

[73] Assignee: Merck & Co., Inc., Rahway, N.J.

[21] Appl. No.: 28,826

[22] Filed: Mar. 23, 1987

Related U.S. Application Data

[62] Division of Ser. No. 762,001, Aug. 2, 1985, Pat. No. 4,686,101.

[51] Int. Cl.$^4$ .................. C07H 15/12; C12P 21/02; C12N 15/00; C12N 1/00
[52] U.S. Cl. .................................. 536/27; 435/91; 435/68; 435/70; 435/172.3; 435/317.1; 435/320; 935/12
[58] Field of Search .................. 435/68, 70, 91, 235, 435/243, 253, 372.33; 536/27; 425/85, 88, 89; 935/12, 32, 37, 57, 65

[56] References Cited
PUBLICATIONS

Ellis et al. (1985) *J. Virology*, vol. 53, pp. 81–88.
Davidson et al. (1985), *J. Gen. Virol.*, vol. 66, pp. 207–220.
Davidson (1983) *EMBO J.*, vol. 2, pp. 2203–2209.

*Primary Examiner*—Thomas G. Wiseman
*Assistant Examiner*—S. Seidman
*Attorney, Agent, or Firm*—Donald J. Perrella; Hesna J. Pfeiffer; Julian S. Levitt

[57] ABSTRACT

A gene of varicella-zoster virus (VZV) which encodes immunogenic outer surface viral proteins has been identified by DNA sequence analysis. This gene can hybrid select messenger RNA which encodes and expresses a protein which reacts with human convalescent zoster sera and with polyclonal monospecific antisera which neutralize viral infectivity. These proteins are useful for the preparation of a vaccine for VZV.

1 Claim, No Drawings

VACCINE AGAINST VARICELLA-ZOSTER VIRUS

This is a division of application Ser. No. 762,001 filed Aug. 2, 1985, now U.S. Pat. No. 4,686,101.

BACKGROUND OF THE INVENTION

Chickenpox is caused by varicella-zoster virus (VZV), a member of the herpesvirus group. The disease occurs in persons with no prior VZV immunity. VZV-specific antibodies can be demonstrated shortly after onset of disease, decline during convalescence, but remain detectable for many years and correlate with immunity to the disease. Chickenpox is highly contagious; over 90% of the population becomes exposed to VZV before they are 20 years old. In most, if not all cases, VZV apparently becomes latent in dorsal root ganglion cells. From this latent state, VZV can reactivate and cause zoster even in the presence of specific antibodies, probably as a result of weakened cellular immunity. The disease is highly morbid to the immunosuppressed and to those beyond the second decade.

VZV has five major glycoproteins on its surface: gp115 (115,000 dalton glycoprotein), gp105, gp92, gp83, gp55. These glycoproteins apparently are the products of three genes: gA (gp105), gB (gp115, in the non-reduced state, composed of the reduced species gp62 and gp57), and gC (gp92, gp83, gp55). Monoclonal antibodies to gA and gB display complement-independent neutralization, and monoclonal antibodies to gC display complement-dependent neutralization.

OBJECTS OF THE INVENTION

It is an object of the present invention to provide antigens which will prevent diseases associated with VZV infections. Another object is to provide antigens which can be used diagnostically to measure VZV antibody titers. Another object is to provide methods for the preparation of these antigens. Another object is to provide methods for using the antigens to raise antibodies, both in vivo and in vitro, to VZV. Another object is to describe the full sequence of protein antigens which will include peptide antigens which may be synthesized by other means or expressed in expression vectors. These and other objects of the present invention will be apparent from the following description.

SUMMARY OF THE INVENTION

The DNA sequence of the VZV gB gene has been identified. A fragment of this sequence has been used to hybrid-select mRNA from VZV-infected cells. In vitro translational products from this mRNA have been immunoprecipitated by guinea pig antibodies raised to gB purified by monoclonal antibody affinity chromatography. Such proteins are useful for the preparation of a vaccine to VZV.

DETAILED DESCRIPTION OF THE INVENTION

The present invention is directed to the identification of the VZV DNA segment which encodes the protective immunogenic gB glycoproteins. More specifically, it is directed to a 2.6 Kilobase pair (Kbp) DNA fragment whose respective nucleotide sequence and derived amino acid sequences have been located within the known sequence of the entire VZV genome.

The present invention also is directed to vectors containing all or part of this 2.6 Kbp DNA fragment. The invention also is directed to host cells which contain these vectors and which cells are capable of expressing all or part of the peptides encoded by the 2.6 Kbp fragment. In accordance with known techniques, it will be obvious to those skilled in the art that parts of the foregoing peptides could be chemically synthesized or modified and retain their immunogenicity. Therefore, the present invention also is directed toward chemical synthesis of domains of these proteins, especially domains including and surrounding hydrophilic regions and threonine or serine and asparagine-X-serine or asprargine-X-threonine residues wherein X is any amino acid residue, since these domains are likely to reside on the outer surface of the virus.

The DNA segment which encodes RNA translatable to gB polypeptides is identified precisely as follows:

Several viral glycoproteins, gp115, gp62 and gp57 (also referred to as gp1 and gp3 or "disulfide-linked dimer") are crossreactive with monoclonal antibodies and have been proposed to be the products of the gB glycoprotein gene. In order to map this gene on the VZV genome, plasmids from a VZV genomic DNA libary have been used to hybrid-select RNA from VZV-infected cells. In vitro translational products are immunoprecipitated by guinea pig antibodies raised to gB purified by monoclonal antibody affinity chromatography. These antibodies are capable of neutralizing viral infectivity. By this analysis, it is found that a 100 Kilodalton (KD) polypeptide can be immunoprecipitated from mRNA selected by the HindIII-D fragment. DNA seqeuence analysis of this region of the VZV genome reveals a 2.6 kbp open reading frame (ORF) which could encode a 100 KD protein with a glycoprotein-like structure (hydrophobic leader, hydrophobic anchor, 9 N-glycosylation recognition sites). This ORF DNA is cloned from the HindIII-D fragment and shown capable of hybrid-selecting mRNA with a 100 KD translational product. Furthermore, the immunoprecipitability of the 100 KD species can be blocked specifically by immune-affinity purified gB. In addition, VZV gB has been purified by immune-affinity chromatography. When injected to guinea pigs, this protein is capable of eliciting the formation of antibodies which neutralize VZV infectivity in vitro. Partial amino acid sequence analysis of the purified VZV gB reveals identity to the amino acid sequence imputed from the DNA sequence of the 2.6 kbp ORF. We conclude that this ORF in the HindIII-D fragment is the glycoprotein gB gene and specifies a gene product carrying neutralization epitopes.

In accordance with known techniques, it will be obvious to those skilled in the art that all or part of the above-mentioned DNA fragment can be placed into an expression vector system in order to produce all or part of the protective immunogenic polypeptide. Such an expression vector system often consists of a plasmid which is inserted into a prokaryotic or eukaryotic cell in order to direct expression of a foreign polypeptide. Such a plasmid usually contains sequences for selection of host cells containing the plasmid, for amplification of plasmid copy number within the host cell, for initiation of transcription of the foreign polypeptide, for termination of transcription of the foreign polypeptide, in addition to the coding sequence per se which specifies the foreign polypeptide. Therefore, the present invention also is directed to host cells and vectors containing all or part of the 2.6 Kbp DNA fragment.

Examples of suitable hosts for expression of VZV proteins include prokaryotic organisms, such as E. coli and B. subtilis, and eukaryotic organisms such as S. cerevisiae and continuous mammalian cell lines including but not limited to Chinese Hamster Ovary cells and Vero cells.

These proteins are useful individually or in combination when placed in a physiologically acceptable carrier, e.g., saline or phosphate buffered saline, to protect against VZV disease when administered to a member of a susceptible mammalian species, in amount of approximately 5 to 150 mcg per dose, preferably from approximately 10 to 50 mcg per dose. One or more doses may be administered to produce effective protection against VZV disease. The protein may be administered by injection, e.g., subcutaneously or intramuscularly. It is also to be understood that these proteins can be directly expressed in humans by means of appropriate viral expression vectors such as adeno, vaccinia, or herpes simplex.

The following examples illustrate the present invention without, however, limiting the same thereto. The disclosure of each reference mentioned in the following examples is hereby incorporated by reference.

EXAMPLE I

DNA fragment which can select RNA encoding the precursor protein to gB glycoproteins Cytoplasmic RNAs were prepared from VZV-infected MRC-5 cells as described in (J. M. Chirgwin et al., Biochemistry 18: 5294 (1979)). The RNAs encoded by the different VZV HindIII fragments were selected by hybridization to cloned VZV HindIII DNA fragments (J. R. Ecker & R. W. Hyman, Proc. Natl. Acad. Sci. USA 79: 156 (1982)) bound to nitrocellulose (J. A. Cooper et al., J. Virology 37: 284 (1981)). These RNAs were translated in a rabbit reticulocyte lysate. The polypeptide products were immunoprecipitated by polyclonal monospecific guinea pig antibodies raised to gB purified by monoclonal antibody affinity chromatography. (This purification is described below in Example V). By this analysis, it was found that a 100 KD in vitro translational product from mRNA selected by the VZV HindIII-D fragment could be immunoprecipitated by the anti-gB antibodies which neutralize viral infectivity. (The neutralization data are described below in Example IV).

EXAMPLE II

DNA fragment of HindIII-D DNA containing a large ORF

Sequence analysis of the HindIII-D fragment from the VZV genome revealed an ORF which could encode a 100 KD protein with a glycoprotein-like structure (hydrophobic leader, hydrophobic anchor, 9 N-glycosylation recognition sites). A segment of this ORF DNA was cloned from the HindIII-D fragment and shown capable of hybrid selecting mRNA with a 100 KD translational product which was immunoprecipitable both by monospecific guinea pig sera and convalescent zoster sera. Furthermore, the immunoprecipitability by both sera of the 100 KD species could be blocked specifically by immune-affinity purified gB but not by another major VZV glycoprotein. Therefore, this segment of HindIII-D DNA was identified as the gB gene.

EXAMPLE III

Dermination of nucleotide sequences of the 2.6 kbp segment of VZV DNA

The complete nucleotide sequence of the VZV HindIII-D DNA segment contains several large open reading frames. One of these open reading frames is 2.6 kbp in length, encodes a 100 KD protein, and contains the segment described in Example II which encodes VZV gB antigens. The nucelotide sequence for the complete 2.6 kbp segment which encodes the gB glycoprotein is given below:

|     |     |     |     |     |     |     |     | ATG | TTT | GTT | ACG | GCG | GTT |
| --- | --- | --- | --- | --- | --- | --- | --- | --- | --- | --- | --- | --- | --- |
| GTG | TCG | GTC | TCT | CCA | AGC | TCG | TTT | TAT | GAG | AGT | TTA | CAA | GTA |
| GAG | CCC | ACA | CAA | TCA | GAA | GAT | ATA | ACC | CGG | TCT | GCT | CAT | CTG |
| GGC | GAT | GGT | GAT | GAA | ATC | AGA | GAA | GCT | ATA | CAC | AAG | TCC | CAG |
| GAC | GCC | GAA | ACA | AAA | CCC | ACG | TTT | TAC | GTC | TGC | CCA | CCG | CCA |
| ACA | GGC | TCC | ACA | ATC | GTA | CGA | TTA | GAA | CCA | ACT | CGG | ACA | TGT |
| CCG | GAT | TAT | CAC | CTT | GGT | AAA | AAC | TTT | ACA | GAG | GGT | ATT | GCT |
| GTT | GTT | TAT | AAA | GAA | AAC | ATT | GCA | GCG | TAC | AAG | TTT | AAG | GCG |
| ACG | GTA | TAT | TAC | AAA | GAT | GTT | ATC | GTT | AGC | ACG | GCG | TGG | GCC |
| GGA | AGT | TCT | TAT | ACG | CAA | ATT | ACT | AAT | AGA | TAT | GCG | GAT | AGG |
| GTA | CCA | ATT | CCC | GTT | TCA | GAG | ATC | ACG | GAC | ACC | ATT | GAT | AAG |
| TTT | GGC | AAG | TGT | TCT | TCT | AAA | GCA | ACG | TAC | GTA | CGA | AAT | AAC |
| CAC | AAA | GTT | GAA | GCC | TTT | AAT | GAG | GAT | AAA | AAT | CCA | CAG | GAT |
| ATG | CCT | CTA | ATC | GCA | TCA | AAA | TAT | AAT | TCT | GTG | GGA | TCC | AAA |
| GCA | TGG | CAT | ACT | ACC | AAT | GAC | ACG | TAC | ATG | GTT | GCC | GGA | ACC |
| CCC | GGA | ACA | TAT | AGG | ACG | GGC | ACG | TCG | GTG | AAT | TGC | ATC | ATT |
| GAG | GAA | GTT | GAA | GCC | AGA | TCA | ATA | TTC | CCT | TAT | GAT | AGT | TTT |
| GGA | CTT | TCC | ACG | GGA | GAT | ATA | ATA | TAC | ATG | TCC | CCG | TTT | TTT |
| GGC | CTA | CGG | GAT | GGT | GCA | TAC | AGA | GAA | CAT | TCC | AAT | TAT | GCA |
| ATG | GAT | CGT | TTT | CAC | CAG | TTT | GAG | GGT | TAT | AGA | CAA | AGG | GAT |
| CTT | GAC | ACT | AGA | GCA | TTA | CTG | GAA | CCT | GCA | GCG | CGG | AAC | TTT |
| TTA | GTC | ACG | CCT | CAT | TTA | ACG | GTT | GGT | TGG | AAC | TGG | AAG | CCA |
| AAA | CGA | ACG | GAA | GTT | TGT | TCG | CTT | GTC | AAG | TGG | CGT | GAG | GTT |
| GAA | GAC | GTA | GTT | CGC | GAT | GAG | TAT | GCA | CAC | AAT | TTT | CGC | TTT |
| ACA | ATG | AAA | ACA | CTT | TCT | ACC | ACG | TTT | ATA | AGT | GAA | ACA | AAC |
| GAG | TTT | AAT | CTT | AAC | CAA | ATC | CAT | CTC | AGT | CAA | TGT | GTA | AAG |
| GAG | GAA | GCC | CGG | GCT | ATT | ATT | AAC | CGG | ATC | TAT | ACA | ACC | AGA |
| TAC | AAC | TCA | TCT | CAT | GTT | AGA | ACC | GGG | GAT | ATC | CAG | ACC | TAC |
| CTT | GCC | AGA | GGG | GGG | TTT | GTT | GTG | GTG | TTT | CAA | CCC | CTG | CTG |
| AGC | AAT | TCC | CTC | GCC | CGT | CTC | TAT | CTC | CAA | GAA | TTG | GTC | CGT |
| GAA | AAC | ACT | AAT | CAT | TCA | CCA | CAA | AAA | CAC | CCG | ACT | CGA | AAT |
| ACC | AGA | TCC | CGA | CGA | AGC | GTG | CCA | GTT | GAG | TTG | CGT | GCC | AAT |
| AGA | ACA | ATA | ACA | ACC | ACC | TCA | TCG | GTG | GAA | TTT | GCT | ATG | CTC |

-continued

| | | | | | | | | | | | | |
|---|---|---|---|---|---|---|---|---|---|---|---|---|
| CAG | TTT | ACA | TAT | GAC | CAC | ATT | CAA | GAG | CAT | GTT | AAT | GAA | ATG |
| TTG | GCA | CGT | ATC | TCC | TCG | TCG | TGG | TGC | CAG | CTA | CAA | AAT | CGC |
| GAA | CGC | GCC | CTT | TGG | AGC | GGA | CTA | TTT | CCA | ATT | AAC | CCA | AGT |
| GCT | TTA | GCG | AGC | ACC | ATT | TTG | GAT | CAA | CGT | GTT | AAA | GCT | CGT |
| ATT | CTC | GGC | GAC | GTT | ATC | TCC | GTT | TCT | AAT | TGT | CCA | GAA | CTG |
| GGA | TCA | GAT | ACA | CGC | ATT | ATA | CTT | CAA | AAC | TCT | ATG | AGG | GTA |
| TCT | GGT | AGT | ACT | ACG | CGT | TGT | TAT | AGC | CGT | CCT | TTA | ATT | TCA |
| ATA | GTT | AGT | TTA | AAT | GGG | TCC | GGG | ACG | GTG | GAG | GGC | CAG | CTT |
| GGA | ACA | GAT | AAC | GAG | TTA | ATT | ATG | TCC | AGA | GAT | CTG | TTA | GAA |
| CCA | TGC | GTG | GCT | AAT | CAC | AAG | CGA | TAT | TTT | CTA | TTT | GGG | CAT |
| CAC | TAC | GTA | TAT | TAT | GAG | GAT | TAT | CGT | TAC | GTC | CGT | GAA | ATC |
| GCA | GTC | CAT | GAT | GTG | GGA | ATG | ATT | AGC | ACT | TAC | GTA | GAT | TTA |
| AAC | TTA | ACA | CTT | CTT | AAA | GAT | AGA | GAG | TTT | ATG | CCG | CTG | CAA |
| GTA | TAT | ACA | AGA | GAC | GAG | CTG | CGG | GAT | ACA | GGA | TTA | CTA | GAC |
| TAC | AGT | GAA | ATT | CAA | CGC | CGA | AAT | CAA | ATG | CAT | TCG | CTG | CGT |
| TTT | TAT | GAC | ATA | GAC | AAG | GTT | GTG | CAA | TAT | GAT | AGC | GGA | ACG |
| GCC | ATT | ATG | CAG | GGC | ATG | GCT | CAG | TTT | TTC | CAG | GGA | CTT | GGG |
| ACC | GCG | GGC | CAG | GCC | GTT | GGA | CAT | GTG | GTT | CTT | GGG | GCC | ACG |
| GGA | GCG | CTG | CTT | TCC | ACC | GTA | CAC | GGA | TTT | ACC | ACG | TTT | TTA |
| TCT | AAC | CCA | TTT | GGG | GCA | TTG | GCC | GTG | GGA | TTA | TTG | GTT | TTG |
| GCG | GGA | CTG | GTA | GCG | GCC | TTT | TTT | GCG | TAC | CGG | TAC | GTG | CTT |
| AAA | CTT | AAA | ACA | AGC | CCG | ATG | AAG | GCA | TTA | TAT | CCA | CTC | ACA |
| ACC | AAG | GGG | TTA | AAA | CAG | TTA | CCG | GAA | GGA | ATG | GAT | CCC | TTT |
| GCC | GAG | AAA | CCC | AAC | GCT | ACT | GAT | ACC | CCA | ATA | GAA | GAA | ATT |
| GGC | GAC | TCA | CAA | AAC | ACT | GAA | CCG | TCG | GTA | AAT | AGC | GGG | TTT |
| GAT | CCC | GAT | AAA | TTT | CGA | GAA | GCC | CAG | GAA | ATG | ATT | AAA | TAT |
| ATG | ACG | TTA | GTA | TCT | GCG | GCT | GAG | CGC | CAA | GAA | TCT | AAA | GCC |
| CGC | AAA | AAA | AAT | AAG | ACT | AGC | GCC | CTT | TTA | ACT | TCA | CGT | CTT |
| ACC | GGC | CTT | GCT | TTA | CGA | AAT | CGC | CGA | GGA | TAC | TCC | CGT | GTT |
| CGC | ACC | GAG | ATT | GTA | ACG | GGG | GTG | TAA. | | | | | |

The foregoing nucleotide sequences encode the following peptide:

| | | | | | | | | | | | | |
|---|---|---|---|---|---|---|---|---|---|---|---|---|
| | | | | | | | Met | Phe | Val | Thr | Ala | Val |
| Val | Ser | Val | Ser | Pro | Ser | Ser | Phe | Tyr | Glu | Ser | Leu | Gln | Val |
| Glu | Pro | Thr | Gln | Ser | Glu | Asp | Ile | Thr | Arg | Ser | Ala | His | Leu |
| Gly | Asp | Gly | Asp | Glu | Ile | Arg | Glu | Ala | Ile | His | Lys | Ser | Gln |
| Asp | Ala | Glu | Thr | Lys | Pro | Thr | Phe | Tyr | Val | Cys | Pro | Pro | Pro |
| Thr | Gly | Ser | Thr | Ile | Val | Arg | Leu | Glu | Pro | Thr | Arg | Thr | Cys |
| Pro | Asp | Tyr | His | Leu | Gly | Lys | Asn | Phe | Thr | Glu | Gly | Ile | Ala |
| Val | Val | Tyr | Lys | Glu | Asn | Ile | Ala | Ala | Tyr | Lys | Phe | Lys | Ala |
| Thr | Val | Tyr | Tyr | Lys | Asp | Val | Ile | Val | Ser | Thr | Ala | Trp | Ala |
| Gly | Ser | Ser | Tyr | Thr | Gln | Ile | Thr | Asn | Arg | Tyr | Ala | Asp | Arg |
| Val | Pro | Ile | Pro | Val | Ser | Glu | Ile | Thr | Asp | Thr | Ile | Asp | Lys |
| Phe | Gly | Lys | Cys | Ser | Ser | Lys | Ala | Thr | Tyr | Val | Arg | Asn | Asn |
| His | Lys | Val | Glu | Ala | Phe | Asn | Glu | Asp | Lys | Asn | Pro | Gln | Asp |
| Met | Pro | Leu | Ile | Ala | Ser | Lys | Tyr | Asn | Ser | Val | Gly | Ser | Lys |
| Ala | Trp | His | Thr | Thr | Asn | Asp | Thr | Tyr | Met | Val | Ala | Gly | Thr |
| Pro | Gly | Thr | Tyr | Arg | Thr | Gly | Thr | Ser | Val | Asn | Cys | Ile | Ile |
| Glu | Glu | Val | Glu | Ala | Arg | Ser | Ile | Phe | Pro | Tyr | Asp | Ser | Phe |
| Gly | Leu | Ser | Thr | Gly | Asp | Ile | Ile | Tyr | Met | Ser | Pro | Phe | Phe |
| Gly | Leu | Arg | Asp | Gly | Ala | Tyr | Arg | Glu | His | Ser | Asn | Tyr | Ala |
| Met | Asp | Arg | Phe | His | Gln | Phe | Glu | Gly | Tyr | Arg | Gln | Arg | Asp |
| Leu | Asp | Thr | Arg | Ala | Leu | Leu | Glu | Pro | Ala | Ala | Arg | Asn | Phe |
| Leu | Val | Thr | Pro | His | Leu | Thr | Val | Gly | Trp | Asn | Trp | Lys | Pro |
| Lys | Arg | Thr | Glu | Val | Cys | Ser | Leu | Val | Lys | Trp | Arg | Glu | Val |
| Glu | Asp | Val | Val | Arg | Asp | Glu | Tyr | Ala | His | Asn | Phe | Arg | Phe |
| Thr | Met | Lys | Thr | Leu | Ser | Thr | Thr | Phe | Ile | Ser | Glu | Thr | Asn |
| Glu | Phe | Asn | Leu | Asn | Gln | Ile | His | Leu | Ser | Gln | Cys | Val | Lys |
| Glu | Glu | Ala | Arg | Ala | Ile | Ile | Asn | Arg | Ile | Tyr | Thr | Thr | Arg |
| Tyr | Asn | Ser | Ser | His | Val | Arg | Thr | Gly | Asp | Ile | Gln | Thr | Tyr |
| Leu | Ala | Arg | Gly | Gly | Phe | Val | Val | Val | Phe | Gln | Pro | Leu | Leu |
| Ser | Asn | Ser | Leu | Ala | Arg | Leu | Tyr | Leu | Gln | Glu | Leu | Val | Arg |
| Glu | Asn | Thr | Asn | His | Ser | Pro | Gln | Lys | His | Pro | Thr | Arg | Asn |
| Thr | Arg | Ser | Arg | Arg | Ser | Val | Pro | Val | Glu | Leu | Arg | Ala | Asn |
| Arg | Thr | Ile | Thr | Thr | Thr | Ser | Ser | Val | Glu | Phe | Ala | Met | Leu |
| Gln | Phe | Thr | Tyr | Asp | His | Ile | Gln | Glu | His | Val | Asn | Glu | Met |
| Leu | Ala | Arg | Ile | Ser | Ser | Ser | Trp | Cys | Gln | Leu | Gln | Asn | Arg |
| Glu | Arg | Ala | Leu | Trp | Ser | Gly | Leu | Phe | Pro | Ile | Asn | Pro | Ser |
| Ala | Leu | Ala | Ser | Thr | Ile | Leu | Asp | Gln | Arg | Val | Lys | Ala | Arg |
| Ile | Leu | Gly | Asp | Val | Ile | Ser | Val | Ser | Asn | Cys | Pro | Glu | Leu |
| Gly | Ser | Asp | Thr | Arg | Ile | Ile | Leu | Gln | Asn | Ser | Met | Arg | Val |
| Ser | Gly | Ser | Thr | Thr | Arg | Cys | Tyr | Ser | Arg | Pro | Leu | Ile | Ser |
| Ile | Val | Ser | Leu | Asn | Gly | Ser | Gly | Thr | Val | Glu | Gly | Gln | Leu |
| Gly | Thr | Asp | Asn | Glu | Leu | Ile | Met | Ser | Arg | Asp | Leu | Leu | Glu |
| Pro | Cys | Val | Ala | Asn | His | Lys | Arg | Tyr | Phe | Leu | Phe | Gly | His |
| His | Tyr | Val | Tyr | Tyr | Glu | Asp | Tyr | Arg | Tyr | Val | Arg | Glu | Ile |
| Ala | Val | His | Asp | Val | Gly | Met | Ile | Ser | Thy | Tyr | Val | Asp | Leu |
| Asn | Leu | Thr | Leu | Leu | Lys | Asp | Arg | Glu | Phe | Met | Pro | Leu | Gln |

*-continued*

| | | | | | | | | | | | | | |
|---|---|---|---|---|---|---|---|---|---|---|---|---|---|
| Val | Tyr | Thr | Arg | Asp | Glu | Leu | Arg | Asp | Thr | Gly | Leu | Leu | Asp |
| Tyr | Ser | Glu | Ile | Gln | Arg | Arg | Asn | Gln | Met | His | Ser | Leu | Arg |
| Phe | Tyr | Asp | Ile | Asp | Lys | Val | Val | Gln | Tyr | Asp | Ser | Gly | Thr |
| Ala | Ile | Met | Gln | Gly | Met | Ala | Gln | Phe | Phe | Gln | Gly | Leu | Gly |
| Thr | Ala | Gly | Gln | Ala | Val | Gly | His | Val | Val | Leu | Gly | Ala | Thr |
| Gly | Ala | Leu | Leu | Ser | Thr | Val | His | Gly | Phe | Thr | Thr | Phe | Leu |
| Ser | Asn | Pro | Phe | Gly | Ala | Leu | Ala | Val | Gly | Leu | Leu | Val | Leu |
| Ala | Gly | Leu | Val | Ala | Ala | Phe | Phe | Ala | Tyr | Arg | Tyr | Val | Leu |
| Lys | Leu | Lys | Thr | Ser | Pro | Met | Lys | Ala | Leu | Tyr | Pro | Leu | Thr |
| Thr | Lys | Gly | Leu | Lys | Gln | Leu | Pro | Glu | Gly | Met | Asp | Pro | Phe |
| Ala | Glu | Lys | Pro | Asn | Ala | Thr | Asp | Thr | Pro | Ile | Glu | Glu | Ile |
| Gly | Asp | Ser | Gln | Asn | Thr | Glu | Pro | Ser | Val | Asn | Ser | Gly | Phe |
| Asp | Pro | Asp | Lys | Phe | Arg | Glu | Ala | Gln | Glu | Met | Ile | Lys | Tyr |
| Met | Thr | Leu | Val | Ser | Ala | Ala | Glu | Arg | Gln | Glu | Ser | Lys | Ala |
| Arg | Lys | Lys | Asn | Lys | Thr | Ser | Ala | Leu | Leu | Thr | Ser | Arg | Leu |
| Thr | Gly | Leu | Ala | Leu | Arg | Asn | Arg | Arg | Gly | Tyr | Ser | Arg | Val |
| Arg | Thr | Glu | Asn | Val | Thr | Gly | Val. | | | | | | |

EXAMPLE IV

Purification of VZV gB Glycoprotein

Ascites fluids, carrying monoclonal antibody B1 (described in Keller et al., J. Virology 52: 293, 1984), were harvested from mice. An equal volume of 0.15M NaCl was added. Then, a saturated $(NH_4)_2SO_4$ solution was added in an equal total volume and held at 4° C. overnight. This mixture was centrifuged at 10° C. and 2000 rpm. The pellet was resuspended in distilled $H_2O$ (2 mg/ml) and dialyzed overnight against coupling buffer (0.1M $NaHCO_3$, 0.5M NaCl, pH 8.4). One gram of cyanogen bromide-activated Sepharose 4B (Pharmacia, Piscataway, N.J.) was swollen in 0.001N HCl then decanted into a 60 ml coarse sintered glass funnel. This was washed with 200 ml 0.001N HCl, then 50 ml coupling buffer. The Sepharose was then mixed with 10 ml of monoclonal antibody solution and rotated for 2 hours at 23° C. Then, 80 μl ethanolamine was added and the solution was rotated for 1 hour at 23° C. The resin was poured into a disposable chromatography column (BioRad), drained and washed successively with 10 ml volumes of the following solutions: (1) coupling buffer; (2) 0.1M $Na_2HPO_4$; 0.5M NaCl, pH 8.2; (3) 0.1M NaOAc, 0.5M NaCl, pH 4.0; (4) 0.1M $NaHBO_4$, pH 8.2; (5) 3M KSCN; (6) 0.1M $NaHBO_4$, pH 8.2; then stored in 0.1M $NaHBO_4$, pH 8.2 at 4° C. prior to use.

VZV glycoproteins were purified from MRC-5 human diploid fibroblasts which were infected with VZV to the extent of 80% cytopathic effect. Cells in 750 $cm^2$ roller bottles were washed twice with 0.15M NaCl, 0.01M $Na_2HPO_4$, pH 7.2 and drained well. Ten ml of 50 mM Tris, pH 7.5, 2% Triton X-100, 4 mM phenylmethylsulfonylfluoride (PMSF) were incubated 15 minutes to the bottle while rolling. The same 10 ml then were used to successively extract 9 more roller bottles. A fresh 10 ml aliquot of buffer was used to successively rinse the 10 roller bottles and pooled with the first aliquot, such that 20 ml of extract represent material from 10 roller bottles. Extracts were stored at −70° C. until use.

Extracts were thawed and dialyzed overnight at 4° C. against 0.15M NaCl, 0.01M $Na_2HPO_4$, 0.05% Triton X-100, pH 7.2, then clarified by centrifuging at 1500 rpm for 15 minutes at 4° C. 20 ml of extract were added to 1 g of monoclonal antibody-coupled resin and incubated overnight at 4° C. with shaking. The slurry was centrifuged for 15 minutes at 1500 rpm at 4° C. and washed three times with 0.1M $NaHBO_4$, pH 8.2. The glycoprotein was eluted by incubation at 23° C. with 10 ml 3M KSCN. The eluate was immediately dialyzed against 0.15M NaCl, 0.01M $Na_2HPO_4$, 0.05% Triton X-100, pH 7.2 overnight at 4° C. and concentrated to approximately 1 mg/ml.

Of the immune-affinity purified gB, approximately 500 μg was loaded into the sample loop of a LCC (Liquid Chromatography Controller) 500 FPLC (Fast Protein Liquid Chromatography) (Pharmacia). The sample then was injected onto a Mono Q anion exchange column (Pharmacia) followed by a 5 ml wash with 20 mM Tris, pH 7.7, 20 mM CHAPS (Sigma). A gradient of 0–1M NaCl in 20 mM Tris, pH 7.5, 20 mM CHAPS was run over the column, and individual fractions were collected. At approximately 0.3M NaCl, there was eluted a single major homogeneous peak which was concentrated in a Centricon concentrator (Amicon) to a volume of 50 μl in 10 mM Tris, pH 7.5, 10 mM NaCl, 0.05% Triton X-100. This peak was verified as VZV gB by the following criteria. In silver strains of sodium dodecyl sulfate-polyacrylamide gel electrophoresis (SDS-PAGE) run under reducing conditions, the sample was resolved as two proteins of molecular weights 62,000 and 57,000 daltons, as described in Keller et al., ibid., i.e., gp62, gp57; Okuno et al., Virology 129: 357 (1983), i.e., gp5; Grose et al., Virology 132: 138 (1984), i.e., gp66, "disulfide-linked dimer"; Ferghani et al., J. Virology, 52: 55 (1984), i.e., 64K–65K. In silver strains of SDS-PAGE run under non-reducing conditions, the sample was resolved as a single protein of molecular weight 115,000, as described in Grose et al. ibid., i.e., gp140, Vafai et al., J. Virology 52: 953 (1984), i.e., gp130.

EXAMPLE V

Purified VZV gB polypeptide induces antibodies which neutralize VZV infectivity in vitro Guinea pigs were inoculated intramuscularly with 20 micrograms in complete Freund's adjuvant of VZV gB (purified by immune-affinity chromatography as described above in Example IV), followed one month later by two inoculations each of ten micrograms of VZV gB in incomplete Freund's adjuvant spaced two weeks apart. Sera were obtained from the guinea pigs after these three inoculations. Each of the guinea pig sera were utilized in an in vitro VZV neutralization assay as described (Keller et al., ibid.). By this assay the post-immunization but not the pre-immunization sera elicited VZV neutralizing antibodies.

EXAMPLE VI

Amino acid analysis of purified VZV gB polypeptide

300 μg of VZV gB (purified as described in Example IV) was subjected to amino-terminal sequence analysis using an Applied Biosystems Gas-Phase Sequenator [Hewick et al., J. Biol. Chem. 256: 7790 (1981)]. The PTH (phenylthiohydantoin) amino acids produced at each step were separated and quantitated by high performance liquid chromatography [Speiss et al., Proc. Natl. Acad. Sci., USA 70: 2974 (1979)].

The sequence analysis demonstrated that gB contains two distinct amino-termini consistent with the analysis described above in Example IV. Each cycle of the sequenator revealed 0, 1 or 2 identifiable amino acids. In all, 11 amino acids in gB were identified. Six of these could be aligned within the sequence of amino acids 9-20 imputed from the DNA sequence in Example III above. Five of these could be aligned within the sequence of amino acids 432-443 imputed from the DNA sequence in Example III above. Since the imputed amino acid sequence contains 868 amino acids, these sequence data of the purified VZV gB are consistent with a cleavage event that partitions the protein to two polypeptides, each containing approximately 430 amino acids. This is consistent with the closely similar molecular weigths of the two reduced species of VZV gB, i.e., gp62 and gp57.

FIG. 1
Amine acid sequence analysis of purified VZV gB

|   | | | | | | | | | | | | |
|---|---|---|---|---|---|---|---|---|---|---|---|---|
| 1 | val | ser | pro | ser | ser | phe | tyr | glu | ser | leu | gln | val |
| 2 | — | — | pro | — | — | phe | tyr | — | — | leu | gln | val |
|   | — | — | pro | val | — | leu | — | ala | — | — | — | ile |
| 3 | ser | val | pro | val | glu | leu | arg | ala | asn | arg | thr | ile |

1 = imputed amino acids 9-20 from Example III
2 = amino acid sequence of purified VZV gB wherein a dash (—) means that no amino acid was resolved at that position
3 = imputed amino acids 432-443 from Example III

What is claimed is:
1. A 2.6 kbp fragment of VZV DNA having the nucleotide sequence:

ATG TTT GTT ACG GCG GTT
GTG TCG GTC TCT CCA AGC TCG TTT
TAT GAG AGT TTA CAA GTA
GAG CCC ACA CAA TCA GAA GAT ATA
ACC CGG TCT GCT CAT CTG
GGC GAT GGT GAT GAA ATC AGA GAA
GCT ATA CAC AAG TCC CAG
GAC GCC GAA ACA AAA CCC ACG TTT
TAC GTC TGC CCA CCG CCA
ACA GGC TCC ACA ATC GTA CGA TTA
GAA CCA ACT CGG ACA TGT
CCG GAT TAT CAC CTT GGT AAA AAC
TTT ACA GAG GGT ATT GCT
GTT GTT TAT AAA GAA AAC ATT GCA
GCG TAC AAG TTT AAG GCG
ACG GTA TAT TAC AAA GAT GTT ATC
GTT AGC ACG GCG TGG GCC
GGA AGT TCT TAT ACG CAA ATT ACT
AAT AGA TAT GCG GAT AGG
GTA CCA ATT CCC GTT TCA GAG ATC
ACG GAC ACC ATT GAT AAG
TTT GGC AAG TGT TCT TCT AAA GCA
ACG TAC GTA CGA AAT AAC
CAC AAA GTT GAA GCC TTT AAT GAG
GAT AAA AAT CCA CAG GAT
ATG CCT CTA ATC GCA TCA AAA TAT
AAT TCT GTG GGA TCC AAA
GCA TGG CAT ACT ACC AAT GAC ACG
TAC ATG GTT GCC GGA ACC
CCC GGA ACA TAT AGG ACG GGC ACG
TCG GTG AAT TGC ATC ATT
GAG GAA GTT GAA GCC AGA TCA ATA
TTC CCT TAT GAT AGT TTT
GGA CTT TCC ACG GGA GAT ATA ATA
TAC ATG TCC CCG TTT TTT
GGC CTA CGG GAT GGT GCA TAC AGA
GAA CAT TCC AAT TAT GCA
ATG GAT CGT TTT CAC CAG TTT GAC
GGT TAT AGA CAA AGG GAT
CTT GAC ACT AGA GCA TTA CTG GAA
CCT GCA GCG CGG AAC TTT
TTA GTC ACG CCT CAT TTA ACG GTT
GGT TGG AAC TGG AAG CCA
AAA CGA ACG GAA GTT TGT TCG CTT
GTC AAG TGG CGT GAG GTT
GAA GAC GTA GTT CGC GAT GAG TAT
GCA CAC AAT TTT CGC TTT
ACA ATG AAA ACA CTT TCT ACC ACG
TTT ATA AGT GAA ACA AAC
GAG TTT AAT CTT AAC CAA ATC CAT
CTC AGT CAA TGT GTA AAG
GAG GAA GCC CGG GCT ATT ATT AAC
CGG ATC TAT ACA ACC AGA
TAC AAC TCA TCT CAT GTT AGA ACC
GGG GAT ATC CAG ACC TAC
CTT GCC AGA GGG GGG TTT GTT GTG
GTG TTT CAA CCC CTG CTG
AGC AAT TCC CTC GCC CGT CTC TAT
CTC CAA GAA TTG GTC CGT
GAA AAC ACT AAT CAT TCA CCA CAA
AAA CAC CCG ACT CGA AAT
ACC AGA TCC CGA CGA AGC GTG CCA
GTT GAG TTG CGT GCC AAT

-continued

AGA ACA ATA ACA ACC ACC TCA TCG GTG GAA TTT GCT ATG CTC
CAG TTT ACA TAT GAC CAC ATT CAA GAG CAT GTT AAT GAA ATG
TTG GCA CGT ATC TCC TCG TCG TGG TGC CAG CTA CAA AAT CGC
GAA CGC GCC CTT TGG AGC GGA CTA TTT CCA ATT AAC CCA AGT
GCT TTA GCG AGC ACC ATT TTG GAT CAA CGT GTT AAA GCT CGT
ATT CTC GGC GAC GTT ATC TCC GTT TCT AAT TGT CCA GAA CTG
GGA TCA GAT ACA CGC ATT ATA CTT CAA AAC TCT ATG AGG GTA
TCT GGT AGT ACT ACG CGT TGT TAT AGC CGT CCT TTA ATT TCA
ATA GTT AGT TTA AAT GGG TCC GGG ACG GTG GAG GGC CAG CTT
GGA ACA GAT AAC GAG TTA ATT ATG TCC AGA GAT CTG TTA GAA
CCA TGC GTG GCT AAT CAC AAG CGA TAT TTT CTA TTT GGG CAT
CAC TAC GTA TAT TAT GAG GAT TAT CGT TAC GTC CGT GAA ATC
GCA GTC CAT GAT GTG GGA ATG ATT AGC ACT TAC GTA GAT TTA
AAC TTA ACA CTT CTT AAA GAT AGA GAG TTT ATG CCG CTG CAA
GTA TAT ACA AGA GAC GAG CTG CGG GAT ACA GGA TTA CTA GAC
TAC AGT GAA ATT CAA CGC CGA AAT

-continued

CAA ATG CAT TCG CTG CGT
TTT TAT GAC ATA GAC AAG GTT GTG CAA TAT GAT AGC GGA ACG
GCC ATT ATG CAG GGC ATG GCT CAG TTT TTC CAG GGA CTT GGG
ACC GCG GGC CAG GCC GTT GGA CAT GTG GTT CTT GGG GCC ACG
GGA GCG CTG CTT TCC ACC GTA CAC GGA TTT ACC ACG TTT TTA
TCT AAC CCA TTT GGG GCA TTG GCC GTG GGA TTA TTG GTT TTG
GCG GGA CTG GTA GCG GCC TTT TTT GCG TAC CGG TAC GTG CTT
AAA CTT AAA ACA AGC CCG ATG AAG GCA TTA TAT CCA CTC ACA
ACC AAG GGG TTA AAA CAG TTA CCG GAA GGA ATG GAT CCC TTT
GCC GAG AAA CCC AAC GCT ACT GAT ACC CCA ATA GAA GAA ATT
GGC GAC TCA CAA AAC ACT GAA CCG TCG GTA AAT AGC GGG TTT
GAT CCC GAT AAA TTT CGA GAA GCC CAG GAA ATG ATT AAA TAT
ATG ACG TTA GTA TCT GCG GCT GAG CGC CAA GAA TCT AAA GCC
CGC AAA AAA AAT AAG ACT AGC GCC CTT TTA ACT TCA CGT CTT
ACC GGC CTT GCT TTA CGA AAT CGC CGA GGA TAC TCC CGT GTT
CGC ACC GAG ATT GTA ACG GGG GTG TAA.

* * * * *